US006853856B2

(12) United States Patent
Yanof et al.

(10) Patent No.: US 6,853,856 B2
(45) Date of Patent: Feb. 8, 2005

(54) DIAGNOSTIC IMAGING INTERVENTIONAL APPARATUS

(75) Inventors: Jeffrey H. Yanof, Solon, OH (US); Uri Shreter, Beachwood, OH (US); Christopher Bauer, Westlake, OH (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/990,127

(22) Filed: Nov. 21, 2001

(65) Prior Publication Data

US 2002/0087065 A1 Jul. 4, 2002

Related U.S. Application Data

(60) Provisional application No. 60/252,938, filed on Nov. 24, 2000.

(51) Int. Cl.[7] ............................. A61B 5/05; A61B 19/00
(52) U.S. Cl. ....................... 600/417; 600/429; 606/130; 901/31
(58) Field of Search .................................. 600/429, 407, 600/411, 420, 418, 417, 423, 427; 901/31, 39; 606/130, 1, 129, 205; 378/901

(56) References Cited

U.S. PATENT DOCUMENTS

| 4,583,538 A | | 4/1986 | Onik et al. |
| 4,733,661 A | | 3/1988 | Palestrant |
| 4,975,016 A | * | 12/1990 | Pellenc et al. ............... 414/501 |
| 5,213,100 A | | 5/1993 | Summ |
| 5,441,042 A | | 8/1995 | Putman |
| 5,957,933 A | * | 9/1999 | Yanof et al. ................. 606/130 |
| 6,478,028 B1 | * | 11/2002 | Paolitto et al. ............. 128/898 |
| 6,665,554 B1 | * | 12/2003 | Charles et al. .............. 600/427 |
| 6,785,572 B2 | * | 8/2004 | Yanof et al. ................. 600/427 |

FOREIGN PATENT DOCUMENTS

| EP | 1 046 377 A2 | 10/2000 |
| WO | WO 00/28882 | 5/2000 |

* cited by examiner

Primary Examiner—Shawna J. Shaw
(74) Attorney, Agent, or Firm—Thomas M. Lundin (57) ABSTRACT

A medical imaging system for conducting an image-guided medical procedure on a subject and a method for performing the same is provided. The system includes a medical imaging apparatus, such as a CT scanner, magnetic resonance imaging system, or ultrasonic imaging system, etc., for obtaining volumetric images of the subject. Through intervention planning techniques, an interventional procedure on a subject using the volumetric images is determined. A mechanical arm assembly disposed in proximity to the medical imaging apparatus carries out the interventional procedure. The mechanical arm assembly includes a base support, a distal end, a plurality of arm segments, and a plurality of joints between the arm segments for carrying out the interventional procedure. An end-effector is disposed at the distal end of the mechanical arm assembly. The end-effector includes gripping means for selectively gripping and releasing a surgical instrument during the interventional procedure.

17 Claims, 6 Drawing Sheets

DIAGNOSTIC IMAGING INTERVENTIONAL APPARATUS

This application claims the benefit of U.S. Provisional Application No. 60/252,938, filed Nov. 24, 2000.

BACKGROUND

The present invention relates to the medical diagnostic imaging and minimally invasive stereotactic surgery arts. It finds particular application in conjunction with an integrated CT scanner and mechanically guided surgical instruments and will be described with particular reference thereto. It is to be appreciated, however, that the invention is also applicable to guiding surgical instruments in conjunction with magnetic resonance, ultrasonic, and other imaging systems.

It is often desired that interventional medical procedures be as minimally invasive as possible. However, it is also desirable to be able to visualize or otherwise know the relative positions and/or orientations of surgical tools or devices with respect to surrounding anatomy. The latter goal may be achieved by a direct inspection of the anatomy. However, in the case of interior anatomy, direct inspection may be more invasive than desired since relatively large incisions may have to be made to expose or access the interior anatomy for direct inspection.

For example, it is often desirable to sample or test a portion of tissue from human or animal subjects, particularly in the diagnosis and treatment of potentially cancerous tumors, pre-malignant conditions, and other diseases or disorders. Typically, in the case of tumors, when the physician suspects that cancer or an otherwise diseased condition exists, a biopsy is performed to determine if in fact cells from the tumor are cancerous or otherwise diseased. Many biopsies, such as percutaneous biopsies, are performed with a needle-like instrument used to collect the cells for analysis.

In recent years, the performance of interventional medical procedures such as needle biopsies has been enhanced by the use of x-ray imaging, CT scans, continuous CT (CCT), magnetic resonance imaging (MRI), fluoroscopy, single photon emission CT (SPECT), positron emission tomography (PET), and the like. The imaging equipment allows an interventionalist, such as a radiologist, surgeon, physician, or other medical personnel, to track the insertion of interventional devices, such as biopsy needles, in a subject during diagnostic and therapeutic procedures. While such imaging modalities allow procedures to be performed with minimal invasiveness and are helpful to the interventionalist and the patient, they have certain drawbacks.

For example, with some image-guided procedures, e.g., those using CT imaging, the tracking of the needle position is not done in real-time. That is to say, a static image is obtained and the needle position noted therein. Subsequently, the needle is advanced or retracted by a small amount and another static image obtained to verify the new needle position. This sequence is repeated as many times as necessary to track the needle's progression. Such a procedure tends to be time consuming insomuch as the needle progresses by only a short distance or increment between imaging, and needle progression is halted during imaging. Moreover, accuracy suffers to the extent that in the interim, i.e., between images, the needle's position cannot be visualized.

With the development of CCT imaging and fluoroscopy, real-time imaging has been made possible. In CCT scanning, a rotating x-ray source irradiates the subject continuously, generating images at a rate of approximately six frames per second. The use of CCT or fluoroscopy by the interventionalist for real-time guidance and/or tracking of the needle during biopsies is gaining popularity. As a result, biopsies have become not only more accurate, but also shorter in duration.

Heretofore, several surgical instrument guidance devices have been proposed for use in conjunction with a CT scanner to allow a user to accurately place a catheter, drainage tube, or biopsy probe within a patient's body. U.S. Pat. No. 4,733,661 describes a hand held guidance device including a planar base with a bubble level to maintain the base in a horizontal position. Needle guides are provided on a support arm pivotally secured to the base, the guides slidingly supporting a catheter at a desired angle as the catheter into the patient's body. The guidance device includes a reference line formed upon the base adapted to be aligned with a transverse light beam projected by the CT scanner apparatus. Although it may be possible for the device to be used to accurately insert a biopsy needle within a patient's body without damage to any unintended targets, one major disadvantage of the device is its reliance upon an accurate human alignment between the reference line defined on the base of the device and the transverse light beam projected by the CT scanner. It would, therefore, be desirable to provide a surgical instrument guidance device which is not dependent upon a manual alignment step.

U.S. Pat. No. 4,583,538 proposes a free standing biopsy guide that is adapted to hold needles or probes at various selectable calculated angles. In using the device proposed in that patent, a reference point on the patient's body is found that exactly correlates to a point on the CT scan. This is accomplished by means of a localization device placed on the patient's skin which can be identified in cross section on the CT scan. Measurements of the localization device on the CT scan are then correlated to the device on the patient. The free standing biopsy guide is then adjusted according to those calculations. One disadvantage of the device taught by this patent is the time required to correlate the patient body reference point with selected points on the CT scan. In addition, certain inaccuracies may be introduced during the point correlation step and while adjusting the free standing guidance device. Accordingly, it would be desirable to provide a biopsy or other surgical instrument guide that is affixed in a known position relative to the CT scanner apparatus whereby precise and automatic correlation between the coordinate systems of the guidance device, patient table, and patient image volume are automatically established.

Another drawing to prior mechanical linkage-type systems relates to the fact that they typically move the needle, or other surgical instrument, along a straight line. Maintaining a straight line can be problematic if the distance to be traveled, i.e. the depth of insertion, by the biopsy needle is large. It is therefore desirable that the mechanical system is able to grip, insert, release, and distally re-grip the biopsy needle for further insertion during an interventional procedure. In this manner, the range of motion of the mechanical system is relatively small, and linear, while the depth of the needle insertion is relatively large.

The present invention provides a new and improved interchangeable surgical instrument guidance device and method for using same which overcomes the above-referenced problems and others.

SUMMARY

In accordance with one aspect of the present invention, a medical imaging system for conducting an image-guided medical procedure on a subject is provided. The system includes a medical imaging apparatus for obtaining volumetric images of the subject, means for planning an interventional procedure on a subject using the volumetric images, and a mechanical arm assembly disposed in proximity to the medical imaging apparatus. The mechanical arm assembly includes a base support, a distal end, a plurality of arm segments, and a plurality of joints between the arm segments for carrying out the interventional procedure. The imaging system further includes an end-effector disposed at the distal end of the mechanical arm assembly. The end-effector includes gripping means for selectively gripping and releasing a surgical instrument during the interventional procedure.

In accordance with a more limited aspect of the present invention, the end-effector further includes a first finger portion having a first gripping surface, a second finger portion having a second gripping surface, the first and second gripping surfaces being opposed to one another for applying a gripping force to the surgical instrument. The end-effector also includes a first surgical instrument guide disposed on the first finger portion and extending towards the second finger portion and a second surgical instrument guide disposed on the second finger portion and extending towards the first finger portion.

In accordance with a more limited aspect of the present invention, the medical imaging system further includes incremental movement means for incrementally inserting the surgical instrument along a trajectory into the subject.

In accordance with a more limited aspect of the present invention, the trajectory is linear.

In accordance with a more limited aspect of the present invention, the gripping force has a magnitude that allows the surgical instrument to be manually inserted into the subject.

In accordance with a more limited aspect of the present invention, the first surgical instrument guide applies a first force to the surgical instrument in a direction perpendicular to the first gripping surface and the second surgical instrument guide applies a second force to the surgical instrument in a direction perpendicular to the second gripping surface.

In accordance with a more limited aspect of the present invention, the first force and the second force are substantially zero.

In accordance with another aspect of the present invention, a method of conducting an image-guided medical procedure on a subject is provided, the method includes the steps of generating at least one volumetric image of the subject, planning an interventional procedure on the subject using the at least one volumetric image, gripping a surgical instrument with an end-effector, the end-effector being disposed at a distal end of a mechanical arm assembly, moving the surgical instrument into the subject along a trajectory in accordance with the planned interventional procedure using the mechanical arm assembly, and releasing the surgical instrument.

In accordance with a more limited aspect of the present invention, the method of conducting an image-guided medical procedure further includes the steps of moving the end-effector away from the subject, regripping the surgical instrument, and moving the surgical instrument further along the trajectory.

In accordance with a more limited aspect of the present invention, the trajectory is linear.

In accordance with a more limited aspect of the present invention, the step of gripping includes the steps of applying a gripping force to the surgical instrument using a first gripping surface disposed on a first finger portion of the end-effector and a second gripping surface disposed on a second finger portion of the end-effector, and stabilizing the surgical instrument using a first instrument guide disposed on the first finger portion and a second instrument guide disposed on the second finger portion.

In accordance with a more limited aspect of the present invention, the step of stabilizing the surgical instrument has a stabilizing force in a direction perpendicular to the first and second gripping surfaces associated therewith.

In accordance with a more limited aspect of the present invention, the stabilizing force is substantially zero.

In accordance with another aspect of the present invention, a medical imaging system is provided. The medical imaging system includes imaging means for generating at least one volumetric image of a subject, planning means for planning an interventional procedure on the subject, a mechanical arm assembly disposed in proximity to the imaging means, the mechanical arm assembly having a base support, a plurality of arm segments, a plurality of joints, and a distal end, and an end-effector disposed at the distal end of the mechanical arm assembly. The end-effector includes a first finger portion having a first gripping surface, a second finger portion having a second gripping surface, the first and second gripping surfaces being opposed to one another for applying a gripping force to a surgical instrument. The end-effector also includes a first surgical instrument guide disposed on the first finger portion and extending perpendicularly to the first gripping surface, and a second surgical instrument guide disposed on the second finger portion and extending perpendicularly to the second gripping surface.

In accordance with a more limited aspect of the present invention, the medical imaging system further includes a mechanical arm controller for controlling the mechanical arm such that the surgical instrument moves along a path in accordance with the planned interventional procedure.

In accordance with a more limited aspect of the present invention, the path includes a linear trajectory into the subject.

In accordance with a more limited aspect of the present invention, the movement of the surgical instrument along the path includes relative movement between the surgical instrument and the end-effector along the linear trajectory.

In accordance with a more limited aspect of the present invention, the medical imaging system further includes position tracking means for tracking a position of the surgical instrument.

In accordance with a more limited aspect of the present invention, the first surgical instrument guide includes a first and second prong, the first and second prongs extending past the first gripping surface and the second surgical instrument guide includes a third and fourth prong, the third and fourth prongs extending past the second gripping surface.

One advantage of the present invention is that it provides for a linear trajectory of a surgical instrument into a subject.

Another advantage of the present invention is that it allows for the surgical instrument to be gripped, inserted into a subject, regripped, and inserted further into the subject while maintaining the same trajectory into the subject.

Another advantage of the present invention is that it does not require a human alignment step for inserting the surgical instrument into the subject.

Another advantage of the present invention is that it provides only minimal torque on the surgical instrument in the end-effector.

Another advantage of the present invention is that is can accommodate various surgical instruments.

Another advantage of the present invention is that it can track the depth of a surgical instrument in the patient.

Another advantage of the present invention is that the gripping means can be easily closed (for gripping purposes) and opened for release.

Still further advantages of the present invention will become apparent to those of ordinary skill in the art upon reading and understanding the following detailed description of the preferred embodiments.

DRAWINGS

The invention may take form in various components and arrangements of components, and in various steps and arrangements of steps. The drawings are only for purposes of illustrating a preferred embodiment and are not to be construed as limiting the invention.

DESCRIPTION

Figure 1:
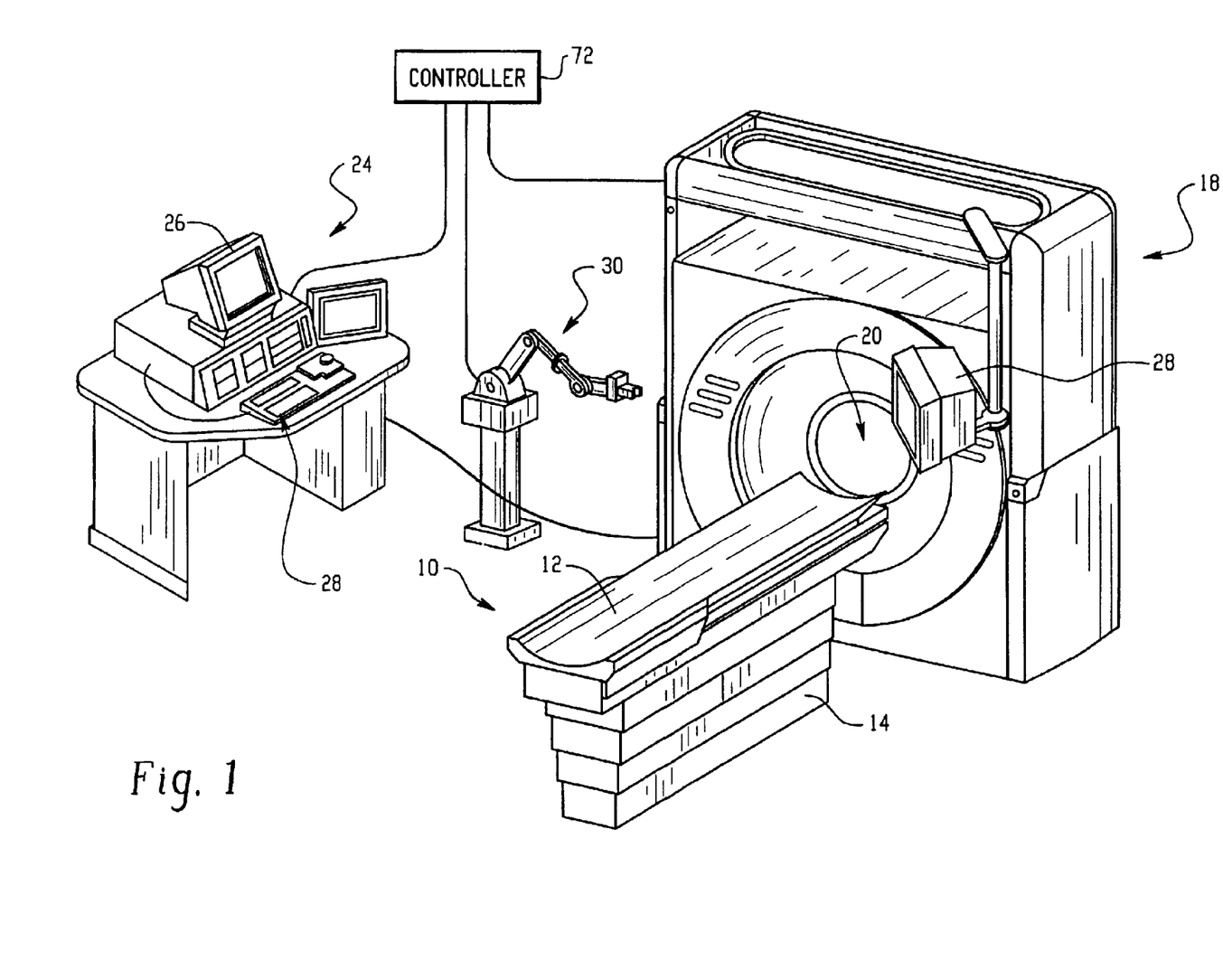
FIG. 1 is a diagrammatic illustration of a CT scanner and surgical instrument guidance device.

With reference first to FIG. 1, a object support 10 such as a patient table includes an object support surface 12 that is mounted for longitudinal movement relative to a base portion 14. The base portion 14 includes a motor for raising and lowering the object support surface 12 and for moving the support surface longitudinally. Position encoders are also provided for generating electrical signals indicative of the height and longitudinal position of the object support.

A volumetric imaging apparatus 18 is disposed in axial alignment with the table such that an object or patient support surface 12 can be moved into and through a bore 20 of the volumetric imager. In the illustrated embodiment, the volumetric imager is a CT scanner which includes an X-ray source (not shown) mounted for repeated circular travel within a preselected plane. The X-ray source projects a fan-shaped beam of radiation through a region of interest of the subject and subsequently to a ring or arc of radiation detectors (not shown) positioned opposite the X-ray source. As the X-ray source rotates about the patient, a series of data lines are generated, which data lines are reconstructed into at least a slice image by a reconstruction processor included in a control console 24. More specifically, the patient support 12 moves longitudinally as the X-ray source is rotating around the subject such that a selected volume of the patient is scanned along a spiral path or a series of slices. The position of the X-ray source is monitored by a rotational position encoder, and the longitudinal position of the patient support is monitored by a longitudinal position encoder within the table 10. The reconstruction processor reconstructs a volumetric image representation from the generated data lines. The control console 24 typically includes one or more monitors 26 and various standard operator input devices, such as a keyboard, trackball, mouse, or the like. An interventionist control console 28 may be supported from overhead on a track atop the CT scanner as shown.

Figure 2:
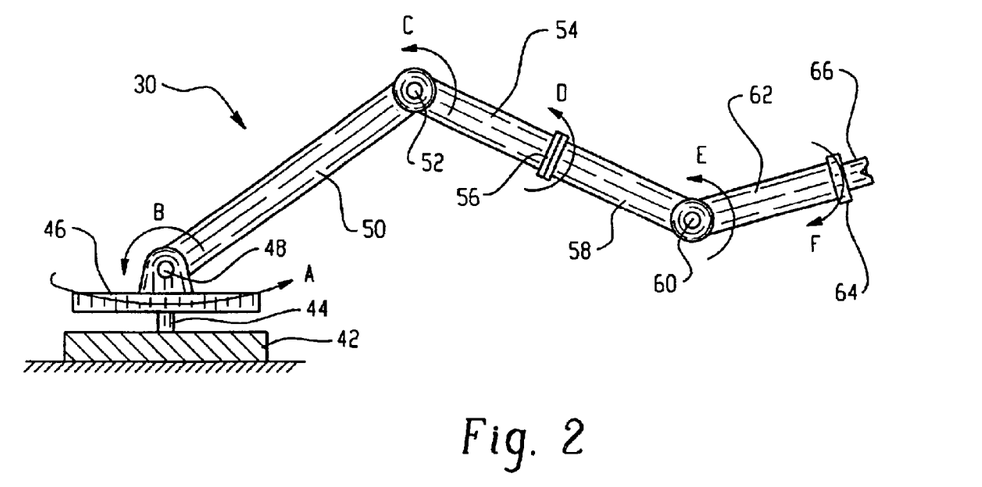
FIG. 2 is a diagrammatic illustration of a mechanical arm assembly carrying an end effector.

Continuing with FIG. 1 and with further reference to FIG. 2, a mechanical arm assembly 30 is located at a known spatial position with respect to the CT scanner. The mechanical arm assembly 30 can be mounted, for example, to the floor, as shown, or to the CT scanner 18 itself. The mechanical arm assembly 30 is controlled by controller 72 and includes a plurality of arm segments which are interconnected by pivot members forming joints between the arm segments. Each pivot member, or joint, includes a drive such as an electric motor which provides a source of motive power for moving each joint to a desired position. Each joint also includes a position encoder such as a quadrature encoder, potentiometer, or the like which provides feedback as to the actual position of the joint. In one embodiment, the joints of the mechanical arm define six (6) degrees of freedom.

With more particular reference to FIG. 2, a base member 42 is located in a known position relative to the CT scanner 18. A base joint 44 permits rotation of a primary support carriage 46 in a direction marked A. Similarly, a first joint 48 permits rotation of a first arm member 50 in a direction marked B, a second joint 52 permits rotation of a second arm member 54 in a direction marked C, and a third joint 56 permits rotation of a third arm member 58 in a direction marked D. A fourth joint 60 permits rotation of a fourth arm member 62 in a direction marked E and a fifth joint 64 permits rotation, in a direction F, of an end-effector 66, such as a gripping device, disposed at the distal end of the mechanical arm assembly 30.

Figure 3A:
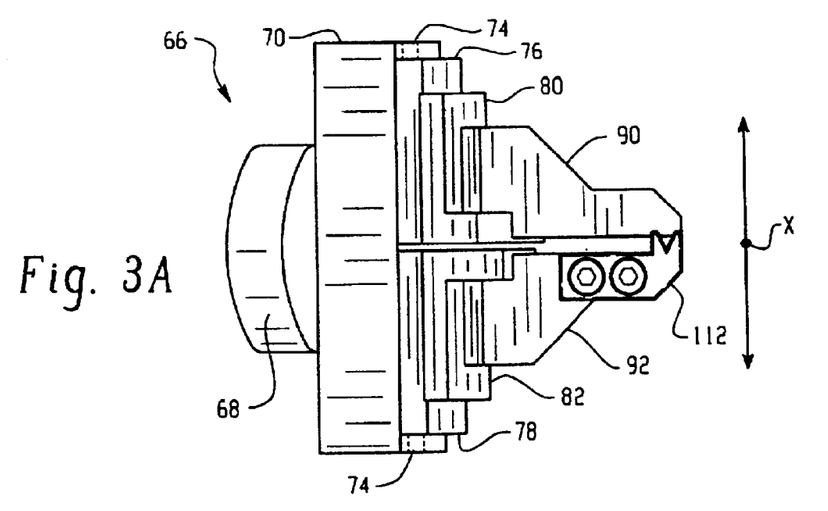
FIG. 3A is a top view of an end effector.
Figure 3B:
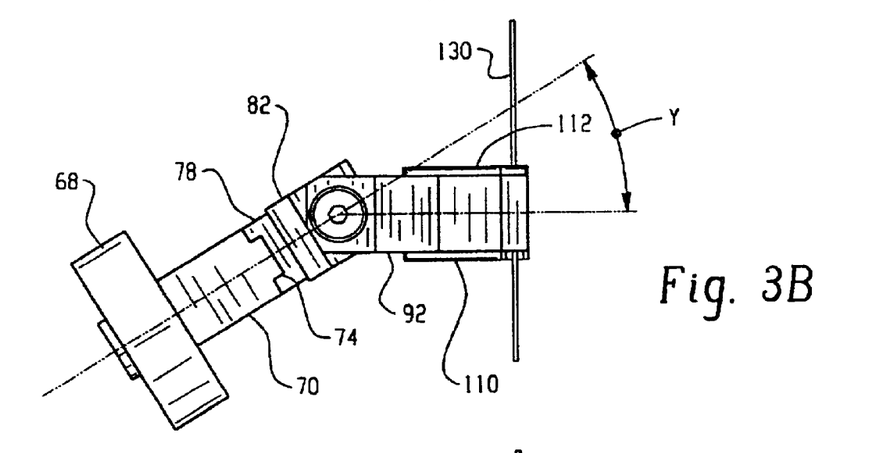
FIG. 3B is a side view of an end effector.
Figure 3C:
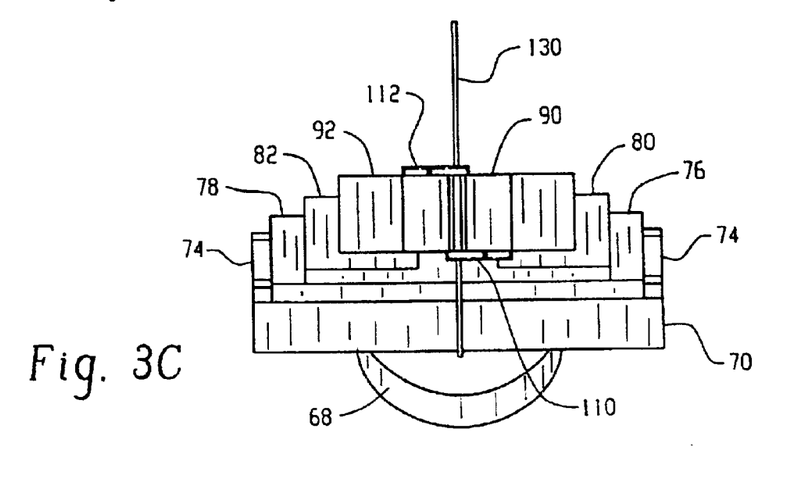
FIG. 3C is a front view of an end effector.

The end-effector 66 is shown generally in FIGS. 3A, 3B, and 3C and includes a base 68 which is attached to the end-effector joint 64. A pneumatic gripper 70 is attached to base 68. The gripper includes a rail 74 upon which grip carriers 76, 78 can be translated toward and away from one another using compressed air, the application of which is controlled by the controller 72. Thus, in the embodiment shown, the grip carriers 76, 78 are movable the direction marked X. The gripper 66 can be, for example, a parallel opening and closing type gripper provided by ZAYTRAN, Inc. Elyria, Ohio, model no. magnum-pet-130-13. While the gripper has been described as a pneumatic controller, other drive types such as electric motors may be implemented. Moreover, the pneumatic driver may use hydraulic fluid or the like. Alternately, the gripper may be operated manually by the interventionist.

L-shaped flanges 80, 82 are attached to the grip carriers 76, 78 respectively. The L-shaped flanges are removeably mounted to the grip carriers such that the base of each flange is parallel with the grip carriers and the portions of the flanges perpendicular to the grip carriers are directed distally from the end-effector joint 64. The flanges 80, 82 translate along with the grip carriers to which they are attached. Fingers 90, 92 are removeably attached to the distally extending portions of the flanges 80, 82, respectively. The fingers can be attached to the flanges with set screws or bolts, for example, such that an angle Y is defined between the longitudinal axes of the fingers and an axis extending distally along the mechanical arm assembly 30 for providing clearance between the mechanical arm 30 and the patient. The fingers translate along with the flanges to which they are attached. In the illustrated closed position, the end effector can be used to grasp an instrument 130 such as a biopsy needle, probe, or the like.

Figure 4:
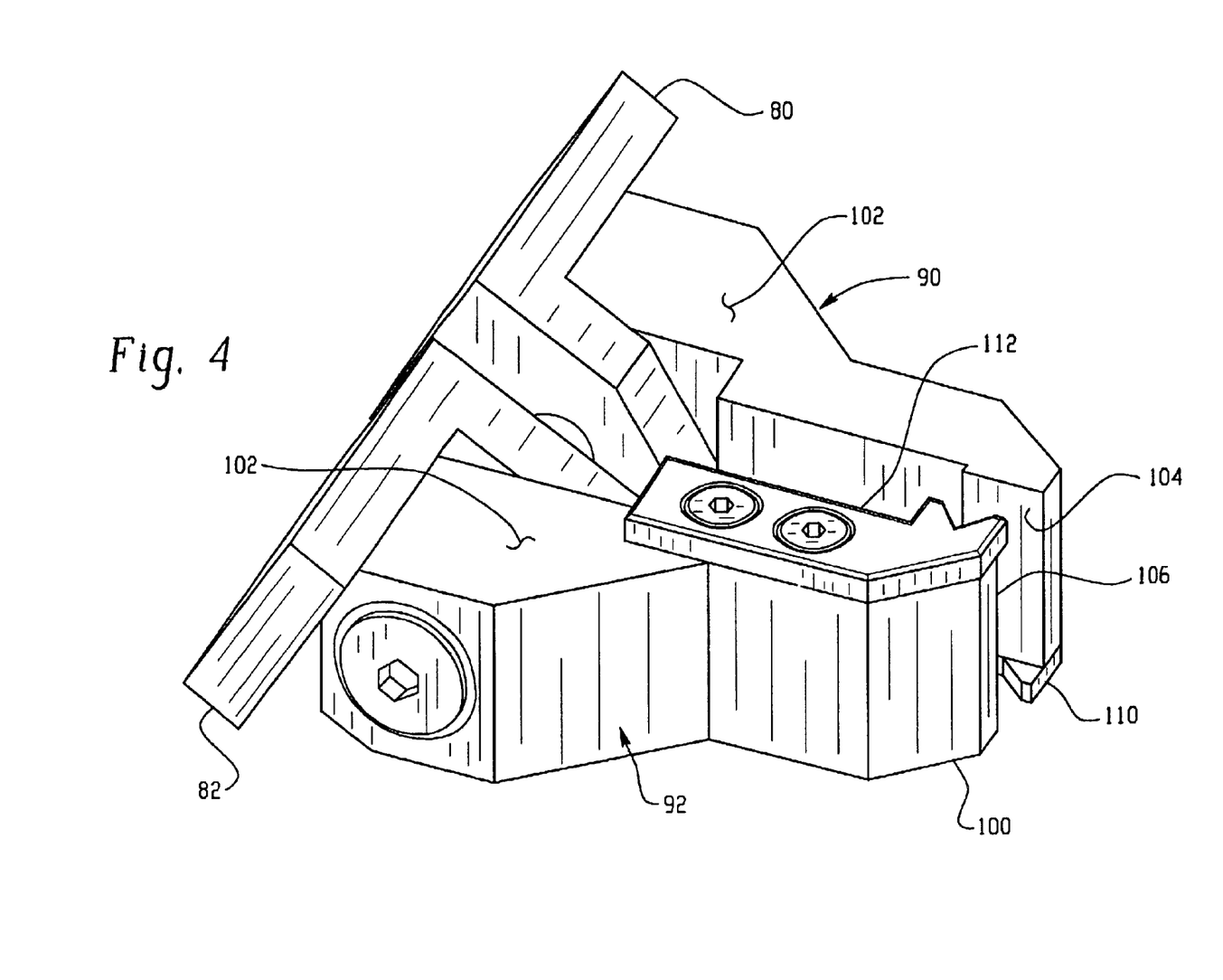
FIG. 4 is a diagrammatic illustration of a pair of gripping fingers.

Turning now to FIG. 4, the fingers of the end effector 66 are shown in an open position. The fingers 90, 92 each include a first surface 100 which, in operation, faces towards the patient and a second surface 102 which faces away from the patient. Gripping surfaces 104, 106 are located at the distal end of the fingers 90, 92 respectively so as to face each other.

In addition to the gripping surfaces 104, 106, substantially v-shaped instrument guides 110, 112 are disposed at the distal end of the fingers 90, 92, respectively. As shown in FIG. 4, the instrument guides are arranged on the fingers such that one of the guides 110 is located on the first surface 100 of the finger 90 and the other guide 112 is located on the second surface 102 of the other finger 92.

Figure 5:
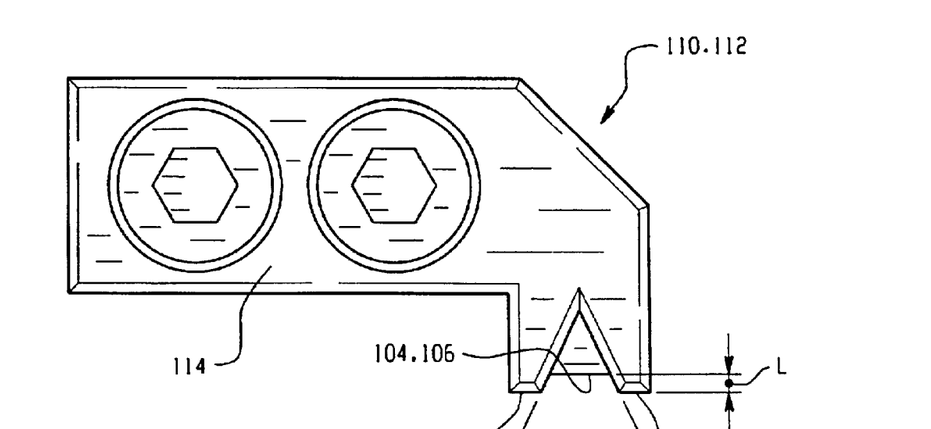
FIG. 5 is a diagrammatic illustration of an instrument guide.

With reference to FIG. 5, each instrument guide 110, 112 includes a body portion 114 which is attached to a given finger 90, 92, and two prongs 120, 122 which extend past the gripping surface 104, 106 of each finger a distance L. The prongs are arranged such that an angle Z is formed between the prongs. The distance L and angle Z are selected such that various sized instruments can be gripped and stabilized by the end effector 66. It is therefore advantageous that the instrument guides 110, 112 are removeably fastened to the fingers 90, 92 so that variously dimensioned instrument guides can be attached to the fingers.

The end-effector 66 can advantageously be fabricated from materials that facilitate use within imaging systems such as CT, MRI and ultrasound systems. In addition, the end-effector can be fabricated from transparent materials such as acrylic so that the instrument 130 can be seen while the end effector is in use.

In operation, volumetric images of a region of interest of a patient are obtained with the CT scanner. The interventionist uses the control console 24 to define a desired position and/or trajectory of the instrument 130 with respect to one or more images displayed thereon. In that the position of the object support 10 (and hence the patient) and the base 42 of the mechanical arm are known in relation to the imaging region of the CT scanner, a desired position of the end effector 66 may be calculated by controller 72 so that an instrument placed in the end effector 66 is diposed at the desired position and/or trajectory.

Once the patient is positioned, the controller 72 drives the motors at each joint of the mechanical arm assembly 30 along a desired trajectory so that the instrument 130 is positioned at the desired location and/or trajectory. In this manner, the surgical instrument 130 is selectively movable in multiple orientations as necessary to position the instrument in various desired positions in relation to the patient. Thus, the instrument can be positioned in predetermined orientations in preparation for and in carrying out a surgical procedure.

Figure 6:
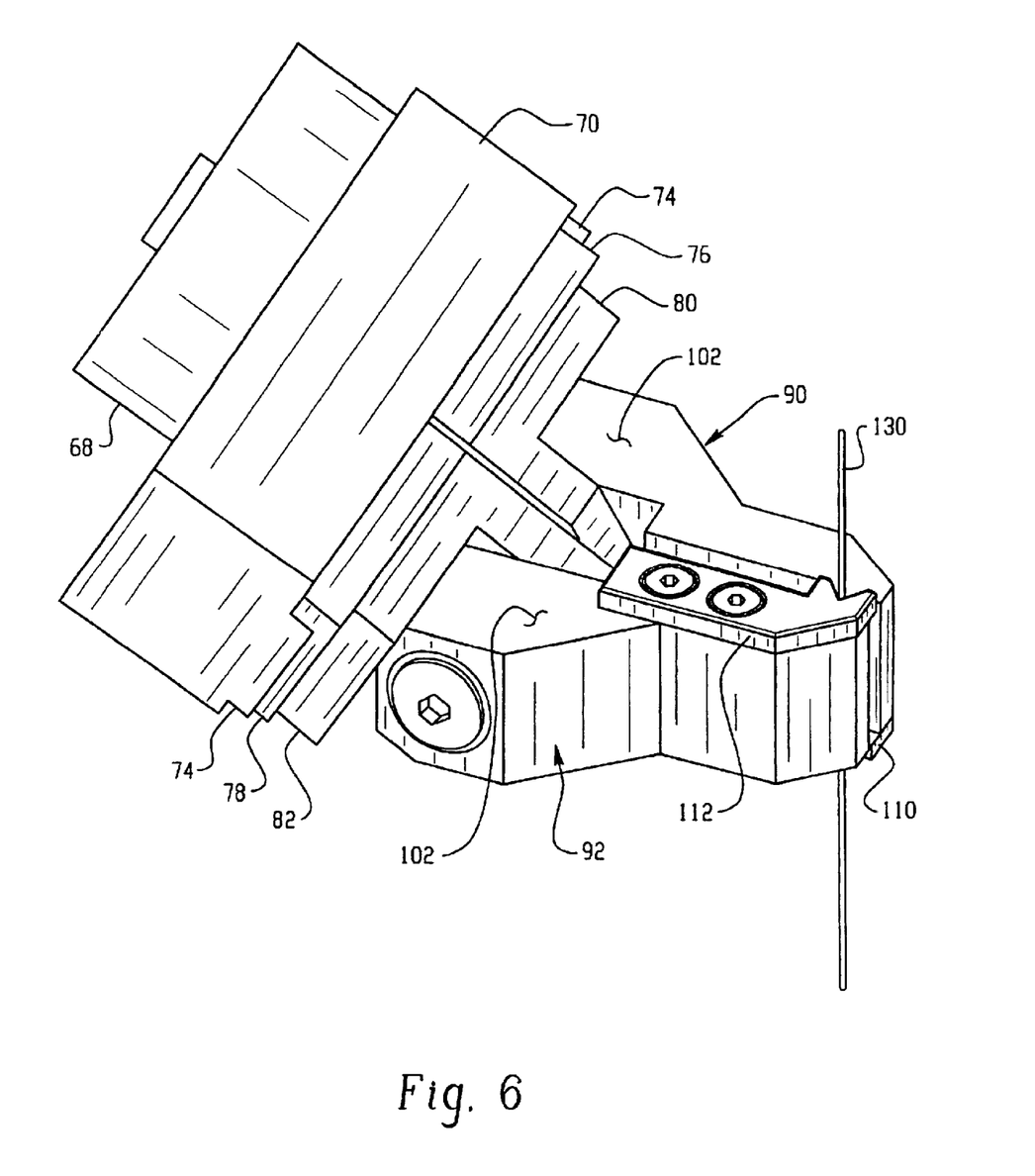
FIG. 6 is a diagrammatic illustration of an end effector carrying an instrument.

As shown in FIG. 6, in the case where the surgical instrument is a biopsy needle, the instrument 130 is located between the gripping surfaces 104, 106 of the fingers. The grip pressure exerted on the instrument 130 by the gripping surfaces 104, 106 is controlled by the controller 72 to prevent or allow relative motion between the needle and fingers as desired. In addition, the instrument 130 passes through the prongs 120, 122 of the instrument guides 110, 112. The prongs provide stability to the instrument and prevent the instrument from rotating away from the desired trajectory line. Additionally, the extension L of the prongs and the angle Z defined therebetween are selected to allow the grip surfaces to contact and grip the instrument while the prongs stabilize the instrument.

Once the mechanical arm 30 has been positioned in the desired location with respect to the patient and the instrument 130 has been secured between the gripping fingers 90, 92, the instrument can be inserted into the patient.

Figure 7:
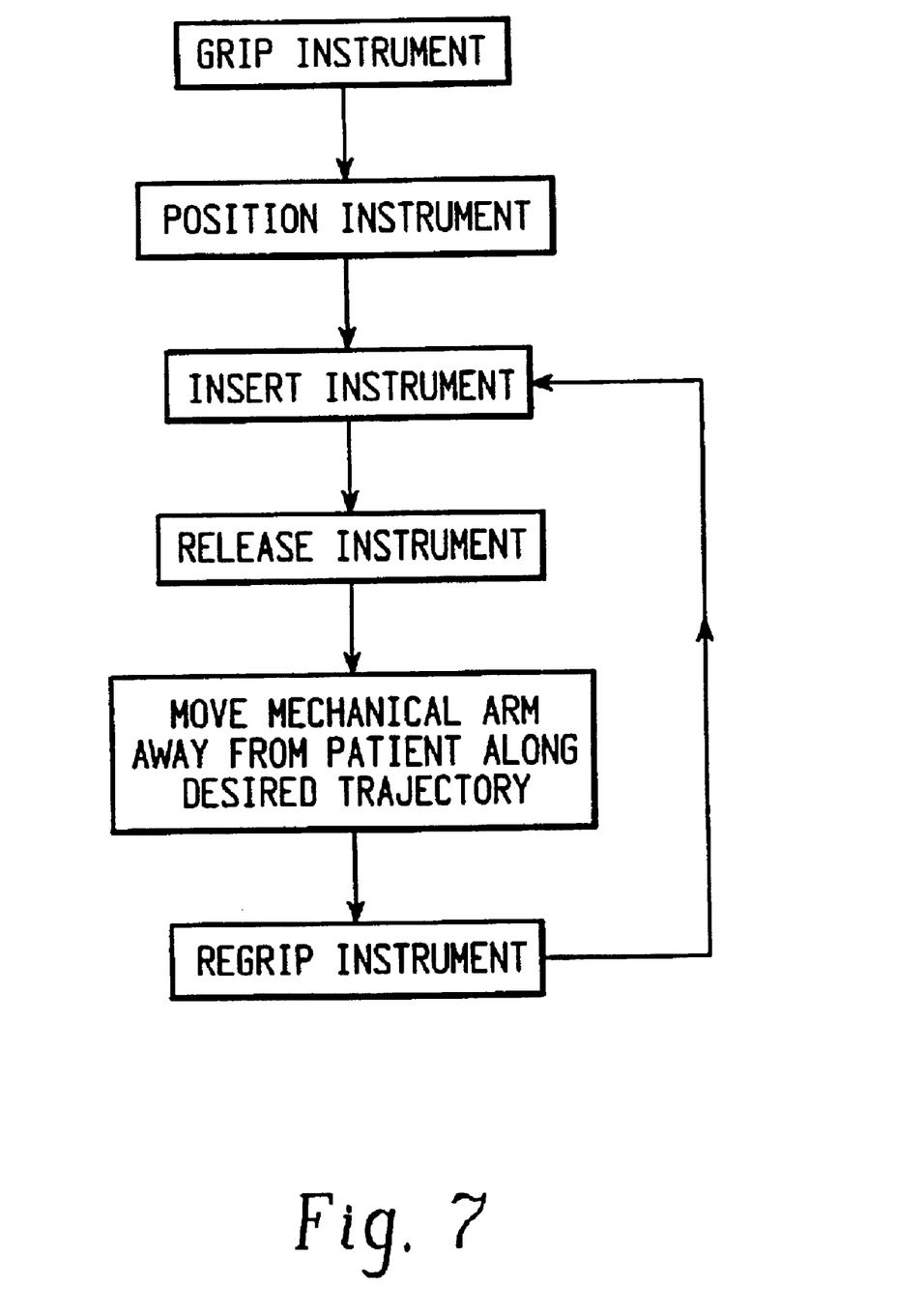
FIG. 7 is a flow chart indicating steps of inserting an instrument into a patient.

In one example, the mechanical arm provides the motive force for inserting the instrument 130 into the patient. In this example, the range of linear motion of the end effector 66 during the insertion process may be limited by the range of motion of the joints of the mechanical arm 30 as well as the distance from the mechanical arm 30 to the patient. In order to overcome this limitation, the instrument can be inserted incrementally by repeating the steps shown in FIG. 7 of inserting the needle into the patient, releasing the grip pressure, moving the mechanical arm away from the patient, regripping the instrument and inserting the instrument further into the patient. During the regripping process, the instrument guides ensure that the instrument is maintained along the desired trajectory. The needle can be removed in a similar manner. Control of the mechanical arm assembly 30 provides that the motion of the needle into the patient is along the desired linear trajectory and that the desired depth of the needle is attained. The linear distance traveled during each increment of insertion or removal is, for example, two centimeters.

The process of releasing grip pressure and regripping the instrument may also be performed without incrementally inserting or removing the instrument. For example, once the instrument is inserted into the patient, the interventionist may desire to manually manipulate the instrument or the patient may need to breathe without the instrument being held securely. Under such circumstances, the instrument may be released and regripped so that the desired trajectory is maintained.

In another example, an interventionist can manually insert the instrument 130 into the patient. In this case, the mechanical arm is stable and is positioned near the patient such that the instrument is oriented along a desired line of insertion into the patient. The grip pressure is set so that the instrument is stable and can still be moved relative to the gripping surfaces by the interventionalist applying a force to the instrument in the direction of insertion. Alternately, an instrument guide can be securely gripped between the grip fingers. The instrument guide defines a bore by which the instrument can be held stable along the insertion line and inserted into the patient.

In another embodiment, a pointing device such as an infrared laser can be gripped by the end effector 66 and held at a distance of, for example, twenty centimeters away from a patient. The pointing device is oriented by the mechanical arm so that it is directed at a region of interest of a patient such as an instrument insertion point and so that its beam is along an insertion trajectory. An interventionist can then position an instrument such as a needle so that its tip is at the insertion point and thereafter rotate the instrument until it is in line with the beam of the pointing device. The interventionist can then insert the instrument as desired while maintaining the trajectory indicated by the pointing device.

In another embodiment, the mechanical arm is manually controlled as described in U.S. Pat. No. 6,035,228, incorporated by reference herein in its entirety.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

What is claimed is:

1. A medical imaging system for conducting an image-guided medical procedure on a subject, the system comprising:

a medical imaging apparatus for obtaining volumetric images of the subject;

means for planning an interventional procedure on a subject using the volumetric images;

a mechanical arm assembly disposed in proximity to the medical imaging apparatus, the mechanical arm assembly comprising a base support, a distal end, a plurality of arm segments, and a plurality of joints between the arm segments for carrying out the interventional procedure; and an end-effector disposed at the distal end of the mechanical arm assembly, the end-effector comprising gripping means for selectively gripping a surgical instrument during the interventional procedure with a gripping force ranging from zero to a force which prevents relative movement between the gripping means and the surgical instrument wherein the end-effector further comprises;

a first finger portion having a first gripping surface;

a second finger portion having a second gripping surface, the first and second gripping surfaces being opposed to one another for applying a gripping force to the surgical instrument;

a first surgical instrument guide disposed on the first finger portion and extending towards the second finger portion; and a second surgical instrument guide disposed on the second finger portion end extending towards the first finger portion.

2. A medical imaging system according to claim 1 further comprising incremental movement means for incrementally inserting the surgical instrument along a trajectory into the subject.

3. A medical imaging system according to claim 2 wherein the trajectory is linear.

4. A medical imaging system according to claim 1 wherein the gripping force has a magnitude that allows the surgical instrument to be manually inserted into the subject.

5. A medical imaging system according to claim 1 wherein the first surgical instrument guide applies a first force to the surgical instrument in a direction perpendicular to the first gripping surface and the second surgical instrument guide applies a second force to the surgical instrument in a direction perpendicular to the second gripping surface.

6. A medical imaging system according to claim 5 wherein the first force and the second force are substantially zero.

7. A method of conducting an image-guided medical procedure on a subject, the method comprising:

generating at least one volumetric image of the subject;

planning an interventional procedure on the subject using the at least one volumetric image;

gripping a surgical instrument with an end-effector, the end-effector being disposed at a distal end of a mechanical arm assembly;

moving the surgical instrument into the subject along a trajectory in accordance with the planned interventional procedure using the mechanical arm assembly; and releasing the surgical instrument wherein the step of gripping comprises the stem of:

applying a gripping force to the surgical instrument using a first gripping surface disposed on a first finger portion of the end-effector and a second gripping surface disposed on a second finger portion of the end-effector; and stabilizing the surgical instrument using a first instrument guide disposed on the first finger portion and a second instrument guide disposed on the second finger portion.

8. A method of conducting an image-guided medical procedure according to claim 7 further comprising the steps of:

moving the end-effector away from the subject;

regripping the surgical instrument; and moving the surgical instrument further along the trajectory.

9. A method of conducting an image-guided medical procedure according to claim 8 wherein the trajectory is linear.

10. A method of conducting an image-guided medical procedure according to claim 7 wherein the step of stabilizing the surgical instrument has a stabilizing force in a direction perpendicular to the first and second gripping surfaces associated therewith.

11. A method of conducting an image-guided medical procedure according to claim 10 wherein the stabilizing force is substantially zero.

12. A medical imaging system comprising:

imaging means for generating at least one volumetric image of a subject;

planning means for planning an interventional procedure on the subject;

a mechanical arm assembly disposed in proximity to the imaging means, the mechanical arm assembly comprising a base support, a plurality of arm segments, a plurality of joints, and a distal end;

an end-effector disposed at the distal end of the mechanical arm assembly, the end-effector comprising:

a first finger portion having a first gripping surface;

a second finger portion having a second gripping surface, the first and second gripping surfaces being opposed to one another for applying a gripping force to a surgical instrument;

a first surgical instrument guide disposed on the first finger portion and extending perpendicularly to the first gripping surface; and a second surgical instrument guide disposed on the second finger portion and extending perpendicularly to the second gripping surface.

13. A medical imaging system according to claim 12 further comprising a mechanical arm controller for controlling the mechanical arm such that the surgical instrument moves along a path in accordance with the planned interventional procedure.

14. A medical imaging system according to claim 13 wherein the path comprises a linear trajectory into the subject.

15. A medical imaging system according to claim 14 wherein the movement of the surgical instrument along the path includes relative movement between the surgical instrument and the end-effector along the linear trajectory.

16. A medical imaging system according to claim 15 further comprising position tracking means for tracking a position of the surgical instrument.

17. A medical imaging system according to claim 12 wherein the first surgical instrument guide comprises a first and second prong, the first and second prongs extending past the first gripping surface and the second surgical instrument guide comprises a third and fourth prong, the third and fourth prongs extending past the second gripping surface.

* * * * *